United States Patent [19]

Tsuchiya et al.

[11] 4,083,954
[45] Apr. 11, 1978

[54] AEROSOL COMPOSITION

[75] Inventors: Yoshimi Tsuchiya, Yachiyo; Yoshinori Naganuma, Hoya; Haruhiko Arai, Narashino, all of Japan

[73] Assignee: Kao Soap Co., Ltd., Tokyo, Japan

[21] Appl. No.: 751,163

[22] Filed: Dec. 16, 1976

Related U.S. Application Data

[63] Continuation-in-part of Ser. No. 670,856, Mar. 26, 1976, abandoned.

[30] Foreign Application Priority Data

Apr. 4, 1975 Japan .................................. 50-40847

[51] Int. Cl.² ................................................ A61K 7/00
[52] U.S. Cl. ...................................... 424/47; 252/305; 424/45; 424/194; 424/324; 424/329; 424/330; 424/343; 424/347; 424/365
[58] Field of Search ..................... 424/45, 47; 252/305

[56] References Cited

U.S. PATENT DOCUMENTS

| | | | |
|---|---|---|---|
| 2,524,590 | 10/1950 | Boe | 252/305 |
| 3,650,981 | 3/1972 | Inouye et al. | 424/45 X |
| 3,719,752 | 3/1973 | Taylor | 424/47 |

*Primary Examiner*—Leonard Schenkman
*Attorney, Agent, or Firm*—Blanchard, Flynn, Thiel, Boutell & Tanis

[57] ABSTRACT

A aerosol composition essentially consists of a starting liquid containing water-alcohol base and an effective or pharmaceutically effective component, a propellant and as an emulsifier an adduct of 1 to 300 moles of ethylene oxide to caster oil, hydrogenated castor oil or lanolin.

16 Claims, No Drawings

AEROSOL COMPOSITION

CROSS-REFERENCE TO RELATED APPLICATION

This application is a continuation-in-part of pending application Ser. No. 670,856, filed Mar. 26, 1976, now abandoned.

BACKGROUND OF INVENTION

1. Field of Invention

The present invention relates to an aerosol composition. More particularly, the invention relates to an aerosol composition having a water-alcohol base which composition is much improved in the emulsion stability.

2. Description of Prior Art

Aerosol products have heretofore been used as glass cleaners, furniture cleaners, other various cleaners, deodorants, insecticides, cosmetics and the like. In these aerosol products, in order to attain a good compatibility with a propellant, solvents such as lower alcohols are used as the base, and effective or pharmaceutically effective components are dissolved or dispersed in these solvents. However, these solvent bases having aerosols are dangerously inflammable, and an expensive, incombustible gas such as Freon (fluorohydrocarbons, the Trade Mark of E. I. Dupont De Nemours & Co.) should be used as the propellant. Further, a component insoluble in a solvent such as ethanol is often used as an effective component. Accordingly, aerosol products in which a water or water-alcohol base is used and a cheap lower hydrocarbon is used as a propellant now attract attention in the art as economical and safe aerosol products.

However, since water and such propellant are incompatible with each other and they differ from each other with respect to the specific gravity, it is very difficult to prepare a homogeneous aerosol from them. More specifically, in an aerosol product comprising a starting liquid of a water base and a propellant, it is very difficult to mix the starting liquid with the propellant uniformly, and the composition gets readily separated into two layers, namely the layer of the starting liquid and the layer of the propellant. As means for overcoming this defect, there has been proposed a method in which several surface active agents are used as an emulsifier to improve the emulsion state between the starting liquid and the propellant. However, satisfactory results could not always be obtained even according to that method because anionic surfactants have corrosive action to a metallic container for the aerosol and nonionic surfactants were also unsatisfactory.

Further, some of the effective or pharmaceutically effective components are water-insoluble. In order to disperse those water-insoluble components stably, a starting liquid having a water-alcohol base containing 30 to 80 wt.% of alcohol, which is formed by adding, for example, a lower alcohol such as methanol, ethanol, and isopropanol to water is preferable, compared with a starting liquid having a water base. In addition, the amount of the emulsifier is preferred to be as small as possible, especially not more than 1 wt.%, in order that the composition may contain a sufficiently large amount of effective components.

However, in an aerosol composition having a water-alcohol base, breaking of the emulsion state between the propellant and the base liquid is more readily caused than in an aerosol composition having the water base alone. Especially in the case of an aerosol composition having a water-alcohol base containing 30 to 80%, especially 40 to 70%, by weight of the alcohol, none of the conventional surface active agents are capable of providing an excellent emulsion state between the base and propellant.

DESCRIPTION OF THE INVENTION

The present inventors have made research works with a view to developing an aerosol composition of the water-alcohol base to give an excellent emulsion stability to a propellant, and they have now completed the present invention. More specifically, in accordance with the present invention, in a pressurized container having a discharge valve and charged with a self-propelling composition which is separated in two phases when said container is allowed to stand and forms a stable homogeneous emulsion of said two phases in said container when said container is shaken and can be dispensed in an aerosol mist form when said discharge valve is opened, the improvement which comprises: said composition consists essentially of A. 15 to 80 wt.% of a liquid propellant effective for discharging an aerosol of the composition when said discharge valve is opened and B. 85 to 20 wt.% of a liquid composition consisting essentially of
   i. 30 to 80 wt.%, based on the weight of B, of an alkanol having one to 3 carbon atoms,
   ii. 0.05 to 1.0 wt.%, based on the weight of B, of an emulsifier consisting of an adduct of 1 to 300 moles of ethylene oxide to a substance selected from the group consisting of castor oil, hydrogenated castor oil and lanolin,
   iii. 0.01 to 20 wt.%, based on the weight of B, of an active component or a mixture of active components and
   iv. the balance is water.

The amount of water is 20 to 70 wt.% based on the weight of B.

In the present invention, by the term the aerosol composition of the water-alcohol base there is meant a composition primarily comprising a starting liquid formed by incorporating a pharmaceutically effective component or other necessary effective component selected according to the intended use in an aqueous solution of a lower alcohol having one to three carbon atoms, such as methanol, ethanol and isopropanol, and a propellant. An aqueous solution of an alcohol may be selected as the medium of the starting liquid according to the kind of a pharmaceutically effective or other necessary, effective component, and the alcohol concentration may be selected within the range of from 30 to 80 wt.%, preferably 40 to 70 wt.%, based on the weight of B. In order to dissolve a water-insoluble active component in the composition, the amount of alkanol must be more than 30 wt.% based on the weight of B and less than 80 wt.%, because the emulsion is otherwise unstable and combustible. The propellant that can be used in the present invention is not particularly critical. In addition to fluorohydrocarbon gases (Freon gas) such as dichlorodifluoromethane and trichloromonofluoromethane, there can be used inflammable lower hydrocarbon gases that are not used in conventional aerosol compositions of the solvent base, such as propane, butane and liquefied petroleum gas (hereinafter referred to as "LPG"), each of which is much cheaper than Freon gases.

An aerosol composition according to this invention contains an active component or a mixture of active components, generally in an amount of 0.01 to 20 wt.% based on the weight of the liquid composition B. A preferable range of the amount is from 0.05 to 10 wt.% and a more preferable range is from 0.1 to 3 wt.%.

A composition according to this invention can be used as a deodorant, hair spray, antiperspirant, antimicrobial, insecticide or insect repellant.

When this aerosol composition is used as a deodorant, 0.1 to 5.0 wt.% of perfume or masking agents may be contained therein, such as alkyl or alkenyl acrylates wherein said alkyl or alkenyl having 8 to 20 carbon atoms, alkyl or alkenyl methacrylates wherein said alkyl or alkenyl having 8 to 20 carbon atoms, dialkyl ($C_4$-$C_8$) fumarate, dialkyl ($C_4$-$C_8$) maleate, 3,5,5-trialkyl ($C_1$-$C_3$) hexanal and geranyl crotonate.

A hair spray composition may contain 0.1 to 10 wt.% of polymer, such as alkyl ($C_1$-$C_3$) polyacrylate, alkyl ($C_1$-$C_3$) polymethacrylate and polyvinylpyrrolidone.

An antiperspirant composition may contain 5 to 20 wt.% of an aluminum compound, such as aluminum chlorohydroxide, aluminum chloride and aluminum sulfocarbonate.

An antimicrobial composition may contain 0.01 to 0.5 wt.% of fungicide or germicide, such as hexachlorophene, dichlorophene, ortho-phenylphenol, 3,4,4'-trichlorocarbanilide, and benzalkonium chloride.

Further, this composition may contain 0.1 to 1.0 wt.% of insecticides, such as pyrethrin of the following formula:

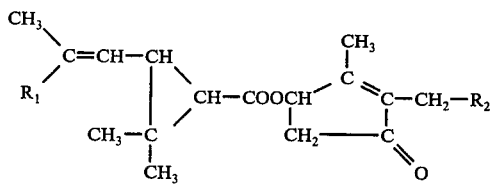

Pyrethrin is called as allethrin when $R_1$ is $CH_3$ and $R_2$ is —CH=$CH_2$; pyrethrin I when $R_1$ is $CH_3$ and $R_2$ is —CH=CH—CH=$CH_2$; pyrethrin II when $R_1$ is $COOCH_3$ and $R_2$ is CH=CH—CH=$CH_2$; cinerin when $R_1$ is $CH_3$ and $R_2$ is —CH=CH—$CH_3$; cinerin II when $R_1$ is $COOCH_3$ and $R_2$ is —CH=CH—$CH_3$; and furethrin when $R_1$ is $CH_3$ and $R_2$ is

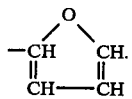

In addition, the insecticide composition containing pyrethrin can be improved by adding 1 to 20 times as much as the weight of pyrethrin added therein of a synergist such as piperonyl butoxide:

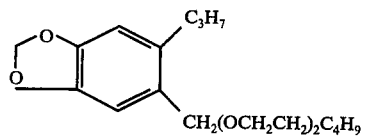

and a compound of the formula:

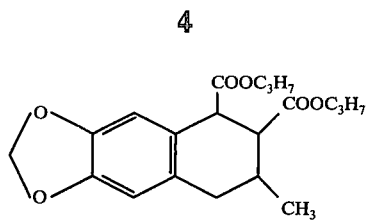

Furthermore, this composition may contain 0.1 to 10 wt.% of an insect repellant such as diethyltoluamide, 2-ethylhexanediol, and the essence extracted from Chrisanthemuna cinerariaefolium Visiana. The above mentioned weight percentages of active components are all based on the weight of the liquid composition B.

In the aerosol composition of the present invention, the mixing weight ratio of the starting liquid to the amount of propellant is generally within the range of from 85/15 to 20/80, preferably 75/25 to 30/70. If the propellant is smaller than 15 wt.%, the composition cannot provide good mist form.

In the aerosol composition of the present invention, an adduct of 1 to 300 moles, preferably 10 to 200 moles, on the average, of ethylene oxide to castor oil, hardened (hydrogenated) castor oil or lanolin is used as the emulsifier together with the above-mentioned starting liquid and propellant. An aerosol composition having an improved and stable emulsion state can be obtained when the emulsifier is incorporated in an amount of 0.05 to 1.0%, preferably 0.1 to 0.7 wt.%, by weight based on the starting liquid. The reason why the amount of the emulsifier should be within the above range is that the effect of an active component can be attained and the self-propellant composition must be dispensed in an aerosol mist form when said discharge valve is opened. In conventional aerosol compositions of the water base, there have heretofore been used as emulsifiers non-ionic surface active agents such as polyoxyethylene alkyl ethers and polyoxyethylene sorbitan fatty acid esters. When these surface active agents are used, it is quite impossible to obtain a stable emulsion state in an aerosol composition of the water-alcohol base. In contrast, in the aerosol composition of the present invention, an improved and stable emulsion state can be attained when the container is shaken in the case of the water-alcohol base. This characteristic feature of the present invention will now be described in detail in reference to the following example. de Emulsion Test Starting liquid (ethanol/water=50/50) : 60% by weight Propellant : 40% by weight A surface active agent indicated in the following table was added to the above starting liquid in an amount of 0.5% by weight, and the mixture was introduced into a transparent vessel, together with the propellant at the above mixing ratio. The emulsion stability of the resulting aerosol composition was examined according to the following test method.

The composition in the vessel was shaken for 15 seconds and then allowed to stand still at room temperature. The time taken for breaking of the emulsion state and phase separation was measured. LPG or dichlorodifluoromethane (F-12) was used as the propellant.

The obtained results are shown in the following table.

The emulsion stability was evaluated on the following scale:

X: phase separation took place in 0 to 5 minutes after shaking.
Δ: phase separation took place in 5 to 30 minutes after shaking.
○: phase separation took place in 30 to 60 minutes after shaking.
⊚: phase separation took place in more than 60 minutes after shaking.

Table

| Surface Active Agent | Propellant LPG | Propellant F-12 |
|---|---|---|
| Controls | | |
| polyoxyethylene alkyl ether ($\bar{K}=12$, $\bar{P}=5$) | X | X |
| polyoxyethylene alkylphenyl ether ($\bar{K}=9$, $\bar{P}=20$) | X-Δ | X |
| polyethylene glycol monolaurate ($\bar{P}=8$) | X | X |
| polyethylene glycol monostearate ($\bar{P}=40$) | X | X-Δ |
| sorbitan fatty acid ester ($\bar{K}=12$) | X | X |
| polyoxyethylene sorbitan fatty acid ester ($\bar{K}=16$, $\bar{P}=20$) | X | X-Δ |
| This Invention | | |
| castor oil-ethylene oxide adduct ($\bar{P}=150$) | ⊚ | ⊚ |
| hydrogenated castor oil-ethylene oxide adduct ($\bar{P}=25$) | ⊚ | ⊚ |
| lanolin-ethylene oxide adduct ($\bar{P}=50$) | ⊚ | ⊚ |
| lanolin-ethylene oxide adduct ($\bar{P}=100$) | ⊚ | ⊚ |

Notes
$\bar{K}$: average carbon number in the alkyl group or fatty acid
$\bar{P}$: average number of moles of ethylene oxide added The aerosol composition of the present invention may be applied to uses for which the conventional aerosol compositions have heretofore been employed, while incorporating therein a pharmaceutically effective or other effective component selected appropriately according to the intended use. For example, the aerosol composition of the present invention can be used for insecticides, various cleaners, hair sprays, paints, deodorants, perspiration-preventing agents, air fresheners, cosmetics and the like.

Typical examples of the present invention will now be described. In these examples, all of "%" and "parts" are by weight.

Example 1
(Deodorant)

| Starting Liquid: | |
|---|---|
| lauryl methacrylate | 0.3% |
| perfume | 1.0% |
| triethylene glycol | 4.0% |
| ethanol | 50.0% |
| hardened castor oil-ethylene oxide adduct ($\bar{P}=25$) | 0.3% |
| ion-exchanged water | balance |
| total | 100.0% |

An aerosol can was filled with 65 parts of the above starting liquid and 35 parts of LPG as a propellant to form an air freshener.

Example 2
(Antiperspirant)

| Starting Liquid: | |
|---|---|
| aluminum sulfocarbonate | 10.0% |
| propylene glycol | 4.0% |
| cetyl alcohol | 1.0% |
| ethyl alcohol | 60.0% |
| fungicide | 0.1% |
| perfume | 0.5% |
| lanolin-ethylene oxide adduct ($\bar{P}\approx100$) | 0.2% |
| ion-exchange water | balance |
| total | 100.0% |

An aerosol can was filled with 60 parts of the above starting liquid and a propellant mixture of 20 parts of dichlorodifluoromethane and 20 parts of dichlorotetrafluoroethane, to form an antiperspirant.

Example 3
(Insecticide)

| Starting Liquid: | |
|---|---|
| pyrethrin | 0.5% |
| phthalthrin | 0.5% |
| piperonyl butoxide | 1.0% |
| petroleum distillate | 5.0% |
| EtOH | 80.0% |
| castor oil ethylene oxide adduct ($\bar{P}\approx100$) | 0.5% |
| ion exchange water | balance |
| total | 100.0% |

An aerosol can was filled with 70 parts by weight of the above starting liquid and 30 parts by weight of a propellant mixture of 60 wt.% of dichlorodifluoromethane and 40 wt.% of dichlorotetrafluoroethane, to form an insecticide agent.

Example 4
(Insect repellent)

| Starting liquid: | |
|---|---|
| diethyl toluamide | 5% |
| perfume | 0.5% |
| EtOH | 70% |
| lanolin ethylene oxide adduct ($\bar{P}\approx100$) | 0.2% |
| | balance |
| total | 100.0% |

Thirty parts by weight of the above starting liquid and 70 parts by weight of a propellant mixture of 50 wt.% of dichlorodifluoromethane and 50 wt.% of dichlorotetrafluoroethane were mixed to form an insect repellant composition.

Example 5
(Germicide or Fungicide)

| Starting liquid: | |
|---|---|
| benzalkonium chloride | 1.0% |
| orthophenylphenol | 0.5% |
| isopropanol | 50% |
| lanolin ethylene oxide adduct ($\bar{P}\approx200$) | 0.1% |
| ion exchange water | balance |
| total | 100.0% |

An aerosol can was filled with 70 parts by weight of the above starting liquid and 30 parts by weight of a propellant mixture of 50 wt.% of dichlorotetrafluoroethane and 50 wt.% of LPG.

Example 6
(Hair-spray)

| Starting liquid: | |
|---|---|
| polyvinyl pyrrolidone | 8.0% |
| cetyl alcohol | 1.0% |
| polyethylene glycol | 1.0% |
| perfume | 0.5% |
| EtOH | 60.0% |
| lanolin ethylene oxide adduct ($\bar{P}\approx50$) | 0.2% |
| ion exchange water | balance |
| total | 100.0% |

An aerosol can was filled with 40 parts by weight of the above starting liquid and 60 parts by weight of a propellant mixture of 25 wt.% of dichlorodifluoromethane and 75 wt.% of dichlorotetrafluoroethane.

When the aerosol compositions obtained in Examples 1 to 4 were tested with respect to the emulsion state, it was found that in each composition, an improved and stable emulsion state was obtained.

The embodiments of the invention in which an exclusive property or privilege is claimed are defined as follows:

1. A pressurized container having a discharge valve and charged with a self-propelling composition, said composition being separated in two phases when said container is allowed to stand, forming a stable homogeneous emulsion of said two phases in said container when said container is shaken and being dispensed in an aerosol mist form when said discharge valve is opened, said composition consisting essentially of
   A. 15 to 80 wt.% of a liquid propellant effective for discharging an aerosol of said composition when said discharge valve is opened and
   B. 85 to 20 wt.% of a liquid consisting essentially of
      i. 30 to 80 wt.%, based on the weight of B, of an alkanol having one to 3 carbon atoms,
      ii. 0.05 to 1.0 wt.%, based on the weight of B, of an emulsifier consisting of an adduct of 1 to 300 moles of ethylene oxide to a substance selected from the group consisting of castor oil, hydrogenated castor oil and lanolin,
      iii. 0.01 to 20 wt.%, based on the weight of B, of an active component or a mixture of active components and
      iv. the balance is water.

2. A pressurized container as claimed in claim 1, in which said propellant is selected from the group consisting of fluorohydrocarbon gases and inflammable lower hydrocarbon gases.

3. A pressurized container as claimed in claim 1, in which said propellant is selected from the group consisting of dichlorodifluoromethane, trichloromonofluoromethane, propane, butane and liquefied petroleum gas.

4. A pressurized container as claimed in claim 1, in which said composition contains, as component (iii), 0.1 to 5.0 wt.%, based on the weight of B, of perfume or masking agent.

5. A pressurized container as claimed in claim 4, in which said perfume or masking agent is selected from the group consisting of alkyl and alkenyl acrylates wherein said alkyl and alkenyl have 8 to 20 carbon atoms, alkyl and alkenyl methacrylates wherein said alkyl and alkenyl have 8 to 20 carbon atoms, dialkyl ($C_4$-$C_8$) fumarate, dialkyl ($C_4$-$C_8$) maleate, 3,5,5-trialkyl ($C_1$-$C_3$) hexanal and geranyl crotonate.

6. A pressurized container as claimed in claim 1, in which said composition contains, as component (iii), 0.1 to 10 wt.% of a polymer selected from the group consisting of alkyl ($C_1$-$C_3$) polyacrylate, alkyl ($C_1$-$C_3$) polymethacrylate and polyvinylpyrrolidone.

7. A pressurized container as claimed in claim 1, in which said composition contains, as component (iii), 5 to 20 wt% of an aluminum antiperspirant compound.

8. A pressurized container as claimed in claim 7, in which said aluminum antiperspirant compound is selected from the group consisting of aluminum chlorohydroxide, aluminum chloride and aluminum sulfocarbonate.

9. A pressurized container as claimed in claim 1, in which said composition contains, as component (iii), 0.01 to 0.5 wt.% of a fungicide or germicide.

10. A pressurized container as claimed in claim 9, in which said fungicide or germicide is selected from the group consisting of hexachlorophene, dichlorophene, orthophenylphenol, 3,4,4'-trichlorocarbanilide, and benzalkonium chloride.

11. A pressurized container as claimed in claim 1, in which said composition contains, as component (iii), 0.1 to 1.0 wt.% of an insecticide.

12. A pressurized container as claimed in claim 11, in which said insecticide is a pyrethrin.

13. A pressurized container as claimed in claim 11, in which said insecticide is selected from the group consisting of a pyrethrin and mixture of a pyrethrin and piperonyl butoxide.

14. A pressurized container as claimed in claim 1, in which said composition contains, as component (iii), 0.1 to 10 wt.% of an insect repellant.

15. A pressurized container as claimed in claim 14, said insect repellant is selected from the group consisting of diethyltoluamide, 2-ethylhexanediol, and the essence extracted from Chrisanthemuna cinerariaefolium Visiana.

16. A pressurized container as claimed in claim 1 containing from 30 to 75 wt.% of A and from 70 to 25 wt.% of B, and wherein the amount of component (i) is from 40 to 70 wt.%, based on the weight of B, the amount of component (ii) is from 0.1 to 0.7 wt.%, based on the weight of B, and said component (ii) is an adduct of from 10 to 200 moles of ethylene oxide to said substance, and the amount of component (iii) is from 0.05 to 10 wt.%, based on the weight of B.

* * * * *